United States Patent [19]

Sabourin et al.

[11] 4,223,172
[45] Sep. 16, 1980

[54] PROCESS FOR THE PREPARATION OF BROMOARYLACETYLENE AND ARYLDIACETYLENE PRECURSORS

[75] Inventors: Edward T. Sabourin, Allison Park; Charles M. Selwitz, Monroeville, both of Pa.

[73] Assignee: Gulf Research & Development Company, Pittsburgh, Pa.

[21] Appl. No.: 967,244

[22] Filed: Dec. 7, 1978

[51] Int. Cl.$^2$ ............... C07C 29/00; C07C 33/10; C07C 33/04
[52] U.S. Cl. ............................ 568/812; 568/807; 568/809; 568/813
[58] Field of Search ............ 568/713, 807, 808, 809, 568/811, 812, 813; 260/646, 6492, R, 650 R

[56] References Cited

U.S. PATENT DOCUMENTS

| 2,693,489 | 11/1954 | Kleinschmidt | 568/813 |
| 3,981,932 | 9/1976 | Diamond | 260/645 |
| 4,089,908 | 5/1978 | Kathawala | 568/813 |

OTHER PUBLICATIONS

Moroz et al. "Izvest. Akad. Nauk SSSR, Ser. Khim" No. 2, pp. 476–479 (1973).
Moroz et al., "C.A." 78:147456x (1973).
Sonogashira et al., "Tetra Letters", No. 50, pp. 4467-4470 (1975) Pergamon Press.
Curtis et al. "Tetra Letters", No. 25, pp. 2919-2920 (1968) Pergamon Press.

*Primary Examiner*—Norman Morgenstern

[57] ABSTRACT

Bromoarylacetylenes such as m-bromophenylacetylene and certain precursors to such bromoarylacetylene are prepared by reacting an aryldibromide with a substituted terminal acetylene compound containing at least three carbon atoms and a hydroxy group on the carbon atom adjacent to the acetylene group in the presence of a dialkyl or trialkyl amine solvent and a catalyst system consisting of a palladium complex containing two halogen moieties and two tri-substituted phosphine moieties. Additional triphenylphosphine can be added. A cuprous iodide promoter is also employed in the reaction sequence. The bromoarylacetylenes can be reacted with a substituted terminal acetylene compound as defined using the same catalyst system as defined to produce the corresponding aryldihydroxy substituted acetylenes. Certain bromophenylhydroxy substituted acetylenes are claimed as new compositions.

7 Claims, No Drawings

PROCESS FOR THE PREPARATION OF BROMOARYLACETYLENE AND ARYLDIACETYLENE PRECURSORS

This invention relates to a process for producing bromoarylhydroxy substituted acetylenes or di(hydroxy substituted acetylene)aromatics and in particular for producing 2-methyl-4-(3-bromophenyl)-3-butyn-2-ol.

BACKGROUND OF THE INVENTION

The recent introduction of acetylene-terminated polyimides to produce cured reaction products which are stable at very high temperatures of 450° C. and up has created an interest and need to produce the polyimides at attractive and competitive costs. The prime difficulty in the preparation of the acetylene-terminated polyimides which are described, for example, in U.S. Pat. Nos. 3,845,018 and 3,879,349, both to Norman Bilow et al, is the preparation of the monomers which include in one instance the preparation of meta-aminophenylacetylene (APA). The process of this invention relates to improved procedures for the preparation of bromoarylacetylenes and in particular to the preparation of bromophenylacetylene, which itself is a precursor to APA.

DESCRIPTION OF THE PRIOR ART

The description of the preparation of APA contained in the teachings of Bilow et al in U.S. Pat. No. 3,845,018 involves a large number of expensive and time-consuming steps. Thus Bilow et al in Column 4, lines 41 et seq., teach that an aromatic compound having both nitro and acetyl substituents is reacted, preferably under reflux, with dimethylformamide and phosphorus oxychloride to convert the acetyl radical to —C(Cl)=CHCHO. The reaction is exothermic, and external cooling is needed to keep it at approximately room temperature. The β-chloro-substituted aldehyde radical is converted to —C≡CH by refluxing a solution of the compound in dioxane and sodium hydroxide. The product is extracted with an organic solvent such as ether; the organic solution is dried; the solvent is removed; and the product recovered by vacuum distillation.

Improved techniques over those taught by Bilow et al obviously have to be developed in order to improve the competitive position of the resultant acetylene-terminated polyimides in the marketplace.

An article entitled, "A Convenient Synthesis of Acetylenes: Catalytic Substitution of Acetylenic Hydrogen with Bromoalkenes, Iodoarenes, and Bromopyridines" by Kenkichi Sonogashira et al, published in Tetrahedron Letters, No. 50, pages 4467–4470, 1975 (Pergamon Press, Gr.Brit.), suggests that iodobenzene could be reacted with acetylene in the presence of a complex catalyst system to produce phenylacetylene. There is no suggestion in the article that bromobenzene or other bromoarenes could be utilized, but only that bromoalkenes or bromopyridines could be substituted for the iodoarene compounds. An attempt was made to react meta-nitrobromobenzene with acetylene using the same catalyst under the same conditions and using the same solvent as taught by Sonogashira et al, but no reaction was observed after six hours, the six hours being the same time period as used by Sonogashira et al for the reaction of acetylene with iodobenzene. Sonogashira et al also present working examples using other acetylenic reactants besides acetylene, namely certain substituted terminal acetylenes, including 2-propyn-1-ol (HC≡C-CH₂-OH) and phenylacetylene. An attempt was then made to react bromobenzene with an analog of 2-propyn-1-ol, i.e. 2-methyl-3-butyn-2-ol using the same conditions as taught by Sonogashira et al, except the temperature was increased from room temperature to 56° C.; and it was found, as will be shown more fully below, that the reaction was extremely sluggish, despite the higher temperature, so that the result was of substantially no interest from a commercial viewpoint.

Earlier work has been done in Russia relating to acetylenic condensation and is contained in an article by M. S. Shvartsberg et al in Izvestiya Akademii Nauk SSSR, Seriya Khimicheskaya, No. 2, pages 476-9 (1973). The Russian work indicates that chloroiodobenzene can be reacted with rather complex substituted acetylenes in the presence of a potassium carbonate—copper catalyst system to produce chlorophenyl substituted acetylenes, which can be hydrolyzed to form less complex substituted chlorophenylacetylenes, which can be further reacted with a weak base to form chlorophenylacetylene. There is no indication or teaching in the Russian article that the bromo analog of the iodochlorobenzene can be employed using the peculiar base catalyst of the Russians. It would thus appear from the prior art that iodobenzene (Sonogashira et al) or chloroiodobenzene (Shvartsberg et al) will work in different catalyst systems with various types of acetylenic or substituted acetylenic charge stocks in such a manner that the acetylenic charge stock substitutes for the iodo group on the benzene nucleus. None of the prior art, however, dictates that bromoarenes can be employed in either of the catalyst systems of the prior art.

Surprisingly, however, and in accordance with the invention, it has been found that bromoarylhydroxy substituted acetylenes can be prepared from an aryldibromide by the reaction of the aryldibromide with a substituted terminal acetylene compound containing at least 3 carbon atoms and a hydroxy group on the carbon atom adjacent to the acetylene group at mild conditions to produce a substantial yield of a bromoarylhydroxy substituted acetylene. The reaction occurs in the presence of an amine-type solvent, which serves not only as a solvent but as a complexing agent with the by-product HBr, which is produced during the reaction. The substitution reaction is catalyzed by a complex palladium salt containing two halogen moieties and two substituted phosphine moieties where the substituents on the phosphorus are phenyl, lower alkyl groups and substituted phenyl groups. The catalytic activity of the palladium complex salt is promoted with a small amount of cuprous iodide.

Any aryldibromide can suitably be employed in the process of this invention. The source of the arylidibromide is not critical and its method of preparation forms no part of this invention.

Preferred are aryldibromides having the formula:

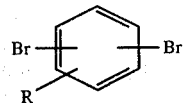

where R can be H, alkyl having from 1 to 10 carbon atoms, preferably 1 to 4 carbon atoms, phenyl, and cycloalkyl having from 5 to 6 carbon atoms.

Suitable non-limiting examples of aryldibromides useful in the process of this invention are:
m-, o- and p-dibromobenzene
2,4-dibromotoluene
2,6-dibromotoluene
2,4-dibromoethylbenzene
2,6-dibromoethylbenzene
2,4-dibromocyclohexylbenzene
2,6-dibromocyclohexylbenzene
2,4-dibromobiphenyl
2,6-dibromobiphenyl
2,3-dibromonaphthalene
1,8-dibromonaphthalene
2,4-dibromopropylbenzene
2,6-dibromohexylbenzene
2,6-dibromononylbenzene
2,4-dibromoisobutylbenzene
2,4-dibromo-6-chloro-toluene The aryldibromide is reacted with a substituted terminal acetylene compound containing at least 3 carbon atoms and a hydroxy group on the carbon atom adjacent to the acetylene group. The preferred substituted terminal acetylene compounds are those having the formula:

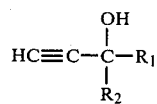

where $R_1$ and $R_2$ can be the same or different and are selected from the group consisting of hydrogen, lower alkyl groups having from 1 to 4 carbon atoms, phenyl, substituted phenyl; or where $R_1$ and $R_2$ can form a saturated 5- or 6-membered ring. The preparation of these compounds is well known in the art and forms no part of the subject invention. For example, acetylene can be reacted with acetone to form 2-methyl-3-butyn-2-ol, which is the preferred substituted terminated acetylenic charge stock for use in the process of this invention. Other suitable acetylenic compounds include the following:

3-methyl-1-pentyn-3-ol;
3-ethyl-1-pentyn-3-ol;
2-phenyl-3-butyn-2-ol;
1-ethynylcyclohexanol; and
1-ethynylcyclopentanol.

The reaction of the aryldibromide with the terminal acetylenic compounds defined above occurs in the presence of a dialkyl or trialkyl amine solvent and a complex catalyst system. The amine solvent can suitably have the formula:

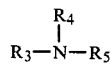

where $R_3$, $R_4$ and $R_5$ can be the same or different and are selected from the group consisting of hydrogen and lower alkyl groups having from 1 to 4 carbon atoms, with the proviso that no more than one of said R groups can be hydrogen. Suitable solvents include but are not limited to dimethylamine, trimethylamine, diethylamine, triethylamine, ethylpropylamine, ethylbutylamine and dibutylamine.

The catalyst employed is a complex palladium salt containing two halogen moieties, where the halogen is selected from the group consisting of bromine, iodine and chlorine, and two trisubstituted phosphine moieties where the constituents are selected from phenyl, alkyl groups having from 1 to 4 carbon atoms, and substituted phenyl groups. A suitable palladium complex would have the formula:

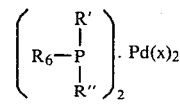

where x is bromine, iodine or chlorine, and $R_6$, $R'$ and $R''$ are the same or different and are selected from the group consisting of phenyl, alkyl groups having from 1 to 4 carbon atoms and substituted phenyl groups. The substituents on the phenyl groups can include alkyl groups having from 1 to 4 carbon atoms, alkoxy groups having 1 to 4 carbon atoms, and halogen. A suitable list of representative palladium complex salts which can be employed in the process of this invention include:

bis(triphenylphosphine)palladium dibromide;
bis(tri-n-butylphosphine)palladium dichloride;
bis(tri-t-butyl-phosphine)palladium dichloride;
bis(tri-i-butylphosphine)palladium dichloride;
bis(triethylphosphine)palladium dichloride;
bis(tripropylphosphine)palladium dichloride;
bis(tritolylphosphine)palladium dichloride;
bis(trianisylphosphine)palladium dichloride;
bis(tri(chlorophenyl)phosphine)palladium dichloride; and
bis(tri(bromophenyl)phosphine)palladium dichloride.

The palladium catalyst can be added to the reaction mixture as such or can be formed in situ in the reaction mixture by the separate addition of a palladium salt having the formula $Pd(x)_2$ where x is as defined, and a trisubstituted phosphine compound having the formula:

where $R_6$, $R'$ and $R''$ are as defined and wherein the molar ratio of the trisubstituted phosphine to the palladium is about 2:1. If desired, the reaction can occur in the presence of excess trisubstituted phosphine, e.g. triphenylphosphine, over and above that necessary to form the palladium catalyst.

Whether the palladium catalyst is formed in situ or whether the palladium catalyst is formed separately and added to the reaction system, the molar ratio of the trisubstituted phosphine compound to palladium in the reaction system is above 2:1, and can suitably be from 2.5:1 to 50:1.

A promoter for the catalyst system is also employed, and this promoter comprises cuprous iodide. Usually the amount of the promoter is very small, and suitable amounts of promoter include a molar ratio of promoter to palladium catalyst of from 0.5:1 to 20:1, preferably from 1:1 to 5:1. The amount of the palladium catalyst employed in the reaction is usually from 0.01 to 1.0 mole percent based on aryldibromide and is more preferably from 0.02 to 0.05 mole percent based on the aryldibromide.

The reaction of the aryldibromide with the acetylene-terminated compound is really a substitution-type reaction, and the reaction conditions to employ are relatively mild and include a temperature from about 20° to 200° C. and more preferably from 50° to 125° C. However, it is considered that the reaction conditions are not critical, and the precise reaction conditions to employ would be obvious to one having ordinary skill in the art. The reaction conditions should be such that the solvent chosen is maintained in the liquid phase. The normal reaction pressure is atmospheric; however, increased reaction pressures of up to 250 psig (1.7MPa) or higher can be employed. The reaction time to employ is somewhat dependent on the particular charge stock and catalyst chosen and, of course, on the reaction temperature. Usually the reaction time is from 1 hour to 150 hours, but is more usually from 3 hours to 24 hours. Higher or lower reaction times can be employed, for timing is not a critical parameter but rather in many cases serves to increase the yield of the desired reaction product.

A typical reaction sequence is shown in Equation 1 below, which utilizes certain specific charge stocks which fall within the scope of the charge stocks defined above.

Equation 1

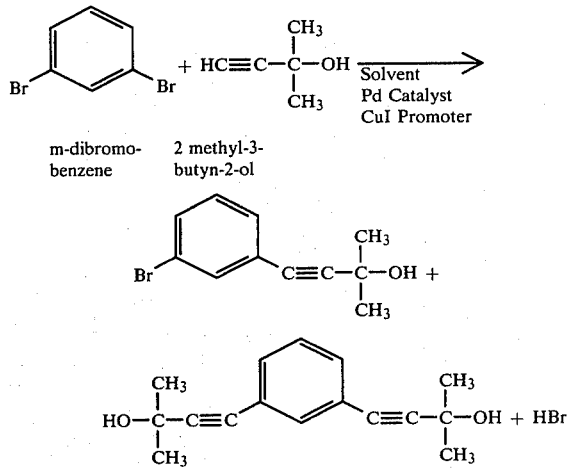

m-dibromo-benzene  2 methyl-3-butyn-2-ol

Referring to Equation 1 above, it can be seen that a byproduct of the reaction sequence is HBr. The HBr cannot be permitted to remain in the reaction product because of its corrosive nature.

It is one of the purposes of the amine solvent to react with the HBr in order to produce the amine hydrobromide salt and render it inactive. The amount of the amine solvent to employ in the reaction is not critical but must thus be sufficient to maintain the reactants in the liquid phase plus provide sufficient amine to react with the byproduct HBr. Amounts of solvent from 500 to 700 ml per mole of dibromobenzene have successfully been employed. However, greater or lesser amounts can be employed, and the particular amount to employ would be within the normal skill in the art given the criteria set forth above.

It can also be seen, referring to Equation 1 above, that both of the bromine groups can be displaced, resulting in the formation of the di(hydroxy substituted acetylene) aromatic compound. The relative proportions of the bromoarylhydroxy substituted acetylene and the diacetylene is a function of the reaction stoichiometry. Thus, when the molar ratio of the terminal acetylene compound to the aryldibromide is about 1:1 or less, substantially the only product is the bromoarylhydroxy substituted acetylene; and as the molar ratio increases above 1:1, increasing amounts of the dihydroxy substituted acetylene aromatic are produced so that at molar ratios of about 2:1, the predominant product is the dihydroxy substituted acetylene aromatic. Thus, if the desired product is the bromoaryl hydroxy substituted acetylene, the molar ratio of the substituted terminal acetylene compound to the aryldibromide is usually from 0.4:1 to 1.5:1 and is preferably from 0.95:1 to 1.05:1. Conversely if the desired product is the di(hydroxy substituted acetylene) aromatic, the molar ratio of the subterminal acetylene compound to the aryldibromide is usually from above 1.5:1 to 4:1 and is preferably from 1.95:1 to 2.1:1.

Of course, the di(hydroxy substituted acetylene) aromatic can be formed by reacting a bromoarylhydroxy substituted acetylene with the defined substituted terminal acetylene compounds and, in this instance, the stoichiometry would dictate molar ratios of about 1:1.

The reaction of the aryldibromide or the bromoarylhydroxy substituted acetylene to produce the di(hydroxy substituted acetylene)aromatic occurs, of course, using the same catalyst system, solvent, and promoter as defined above.

The invention will be further described with reference to the following experimental work.

In all of the experiments to follow, a 3-necked flask equipped with a magnetic stirrer, thermometer, condenser, nitrogen inlet and outlet, a rubber septum sample port and a heating mantle was employed. The flask was charged with the dibromobenzene, the acetylenic charge stock, the catalyst and the amine solvent. The system was then purged with nitrogen for 20 minutes, after which the cuprous iodide was added and the system brought to reaction temperature. Small samples of the reaction mixture were periodically withdrawn by syringe and were subjected to analysis by gas chromatography; and in this manner the reaction was monitored.

Upon termination, the reaction mixture was cooled to room temperature. The reaction solvent was then stripped from the reaction product on a rotary evaporator, followed by the addition of water to the residue to dissolve the salts and any residual amine solvent. Extraction of the aqueous mixture with toluene served to separate the product from the water-soluble components. The organic extract in toluene was then passed through a short column of 200-mesh alumina to remove the palladium catalyst and the cuprous iodide promoter. The toluene was then stripped to provide a crude product. In some cases the product was analyzed at this point by gas liquid chromatography with the aid of mesitylene as an internal standard. In other cases the product was distilled and the distilled product subjected to elemental analysis.

In a first series of runs, m-dibromobenzene

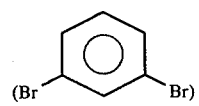

was reacted under a nitrogen atmosphere with 2-methyl-3-butyn-2-ol

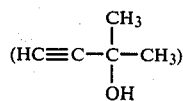

using [(C₆H₅)₃P]₂PdCl₂ as the catalyst, CuI as the promoter, and various amines as solvents at varying reaction conditions. The runs are summarized in Table 1 below:

TABLE 1

Conversion of m-dibromobenzene to 2-methyl-4-(3-bromophenyl)-3-butyn-2-ol

| Ex. No. | Substrate | mmoles | Methyl-butynol mmoles | [(C₆H₅)₃P]₂PdCl₂ mmoles | (C₆H₅)₃P mmoles | CuI mmoles |
|---|---|---|---|---|---|---|
| 1 | Br—◯—Br (meta) | 10 | 10 | 0.07 | — | 0.05 |
| 2 | " | 10 | 36 | 0.07 | — | 0.05 |
| 3 | " | 102 | 101 | 0.07 | — | 0.05 |
| 4 | " | 188 | 187 | 0.07 | — | 0.05 |
| 5 | " | 408 | 428 | 0.21 | — | 0.05 |
| 6 | " | 425 | 510 | 0.07 | — | 0.05 |
| 7 | " | 425 | 440 | 0.07 | 3.8 | 0.05 |
| 8 | " | 425 | 440 | 0.07 | 3.8 | 0.05 |
| 9 | Br—◯—Br (para) | 204 | 202 | 0.07 | — | 0.05 |
| 10 | " | 188 | 392 | 0.14 | — | 0.05 |
| 11 | " | 1000 | 2100 | 0.28 | 7.6 | 0.05 |

| Ex. No. | Substrate | Solvent (amine) ml | Reaction Time hrs. | Reaction Temp. °C. | % Conv. | % Selec. (a) | % Selec. (b) | % Yield (a) | % Yield (b) |
|---|---|---|---|---|---|---|---|---|---|
| 1 | Br—◯—Br (meta) | Diethyl 60 | 3 | 56 | 75.9 | 88.3 | 11.7 | 67.0 | 8.9 |
| 2 | " | Diethyl 60 | 21 | 56 | 100 | 61.0 | 39.0 | 61.0 | 39.0 |
| 3 | " | Diethyl 200 | 21 | 56 | 85.0 | 84.5 | 15.5 | 71.8 | 13.2 |
| 4 | " | Diethyl 300 | 27 | 56 | 82.0 | 85.8 | 14.2 | 70.4 | 11.6 |
| 5 | " | Triethyl 300 | 25 | 90–100 | 83.7 | 74.4 | 25.6 | 62.3 | 21.4 |
| 6 | " | Triethyl 300 | 18.5 | 90–100 | 93.0 | 76.5 | 23.5 | 71.2 | 21.8 |
| 7 | " | Triethyl 300 | 5.5 | 90–100 | 55.0 | 88.4 | 11.6 | 48.6 | 6.4 |
| 8 | " | Triethyl 300 | 21.5 | 90–100 | 84.8 | 84.6 | 15.4 | 71.7 | 13.0 |
| 9 | Br—◯—Br (para) | Diethyl 300 | 93 | 56 | 46.2 | 87.6 | 12.4 | 40.5 | 5.7 |
| 10 | " | Triethyl 200 | 41 | 90–100 | 100 | 12.7 | 87.3 | 12.7 | 87.3 |
| 11 | " | Triethyl 600 | 25 | 90–100 | 93.3 | 33.8 | 66.2 | 31.5 | 61.8 |

(a)This column relates to the selectivity or yield, as appropriate, of bromoaryl hydroxy substituted acetylene, i.e.

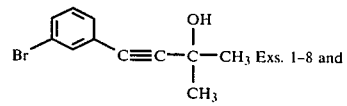

Exs. 1–8 and

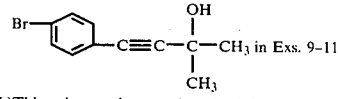

in Exs. 9–11

(b)This column relates to the selectivity or yield, as appropriate, of the di(hydroxy substituted acetylene)aromatic, i.e.

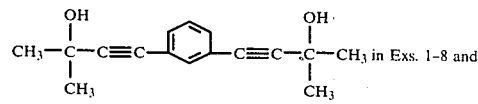

in Exs. 1–8 and

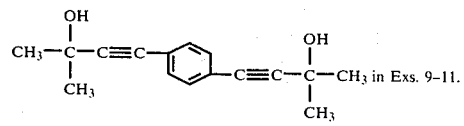

in Exs. 9–11.

Referring to Table 1 above, the Conversion ("Conv.") was a weight percent conversion and was calculated by:

$$\frac{\text{Initial wt dibromobenzene} - \text{Final wt dibromobenzene}}{\text{Initial wt dibromobenzene}} \times 100$$

Selectivity ("Selec.") in Table 1 means, as appropriate:

$$\frac{\text{Moles 2-methyl-4-(3-bromophenyl)-3-butyn-2-ol}}{\text{Initial moles dibromobenzene} - \text{Final moles dibromobenzene}} \times 100$$

or $$\frac{\text{Moles 1,3-di(3-methyl-3-hydroxy-1-butynyl)benzene}}{\text{Initial moles dibromobenzene} - \text{Final moles dibromobenzene}} \times 100$$

The Yield means, as appropriate, the yield of 2-methyl-4-(3-bromophenyl)-3-butyn-2-ol:

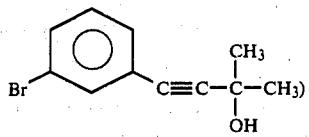

or 1,3-di(3-methyl-3-hydroxy-1-butynyl)benzene:

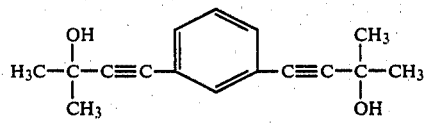

and was calculated as the product of Conversion times Selectivity. Selectivities and yields were calculated only on isolated crude products by gas chromatography with an appropriate internal standard (mesitylene).

Referring again to Table 1, a comparison of Examples 1 and 2 shows the selectivity to and yield of 2-methyl-4(3-bromophenyl)-3-butyn-2-ol decreases as the molar ratio of the 2-methyl-3-butyn-2-ol was increased from 1:1 (Ex. 1) to 3.6:1 (Ex. 2), i.e. the selectivity went from 88.3 to 61.0 and the yield went from 67% to 61%. While the yield decrease was not striking (because the conversion increased from 75.9% to 100%), the "by-product" is mainly to the aryldiacetylene, i.e.

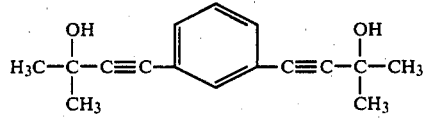

which is made, of course, by the substitution of both bromo groups by the acetylene. Thus, by a proper manipulation of the ratio of the acetylene charge stock to the aryldibromide, the product distribution can be effected to produce more or less of the bromoarylmonoacetylene versus the aryldiacetylene.

Examples 3 and 4 are similar to Example 1 except reaction time is increased, and about the same results are obtained except for higher conversions and yields.

Examples 5 and 6 employ triethylamine as the solvent which allows for the use of higher temperatures (at reflux). For reasons not understood, higher conversion and selectivities were achieved in Example 6 despite a shorter reaction time and the use of less catalyst.

Examples 7 and 8 are similar to Example 6 except excess triphenylphosphine was used. Comparable yields were achieved in Examples 6 and 8, but decreased conversions and yields are realized in Example 7 due to a much shorter reaction time.

Examples 9-11 utilize the para-dibromobenzene, and similar results are obtained to those earlier examples using the m-dibromobenzene. Examples 10 and 11 illustrate the production of primarily the di(hydroxy substituted acetylene) aromatic as a result of increased molar ratios of the methylbutynol to the dibromobenzene.

The bromoarylhydroxy substituted acetylenes produced as described above or the di(hydroxy substituted acetylene) aromatics can be cleaved to produce the corresponding bromoarylacetylene or aryldiacetylene by contacting the bromoarylhydroxy substituted acetylene or di(hydroxy substituted acetylene) aromatic with an alkali metal hydroxide such as sodium hydroxide under mild conditions. Preferably, although not necessarily, the contacting occurs in the presence of an organic solvent, usually aromatic, at the reflux temperature of the solvent, and, of course, with good and adequate mixing.

For example, the 2-methyl-4-(3-bromophenyl)-3-butyn-2-ol can be converted to m-bromophenylacetylene by contact of the former compound with NaOH in toluene as shown in Example 12 below.

EXAMPLE 12

A portion of the product from Example 3 above (2-methyl-4-(3-bromophenyl)-3-butyn-2-ol 5.4 g) was dissolved in 100 ml of toluene containing 0.1 gram of powdered NaOH. The mixture was refluxed for 3 hours. Acetone was removed via a Dean-Stark trip. Gas chromatographic analysis revealed that 100% conversion of the charge stock occurred with 100% selectivity to bromophenylacetylene. Vacuum distillation gave 89% yield of pure product b.p. 86° to 88° C. at 15 mm Hg.

Similarly to Example 12, the di(hydroxy substituted acetylene) aromatic such as 1,3-di(3-methyl-3-hydroxy-1-butyn) benzene can be reacted with NaOH to produce 1,3-diethynyl benzene.

EXAMPLES OUTSIDE THE SCOPE OF THE INVENTION

EXAMPLE 13

Example 1 was repeated except nitrobromobenzene was used in lieu of dibromobenzene, and acetylene was bubbled through. After six hours, no reaction was noted by continuous gas liquid chromatographic analysis.

Example 13 illustrates that acetylene does not react with bromoarenes. This perhaps is not surprising since the teachings of Sonogashira et al are specific to the reaction of acetylene with iodoarenes or bromoalkenes.

EXAMPLE 14

Example 1 was repeated except bromobenzene was the halide employed; the amount of CuI was increased to 0.25 mmol; and the reaction temperature was increased to 56° C. After 116 hours, the conversion was merely 13%. Selectivities and yields were not determined.

Example 14 illustrates that monobromobenzene is a sluggish reactant.

A comparison of Examples 1 and 14 shows the presence of the added bromo group in the dibromobenzene activates the dibromobenzene charge stock so that very high conversions are obtained.

Resort may be had to such variations and modifications as fall within the spirit of the invention and the scope of the appended claims.

We claim:

1. A process for the production of a bromoaryl hydroxy substituted acetylene selected from the group consisting of 2-methyl-4-(3-bromophenyl)-3-butyn-2-ol and 2-methyl-4-(4-bromophenyl)-3-butyn-2-ol which comprises:

reacting an aryldibromide selected from the group consisting of m-dibromobenzene and p-dibromobenzene with 2-methyl-3-butyn-2-ol, wherein the molar ratio of said 2-methyl-3-butyn-2-ol to said aryldibromide is in the range of 0.4:1 to 1.5:1, in the presence of a solvent comprising a compound having the formula:

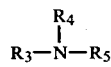

where $R_3$, $R_4$ and $R_5$ can be the same or different and are selected from the group consisting of hydrogen and lower alkyl groups having from 1 to 4 carbon atoms with the proviso that no more than one of said R groups can be hydrogen, and in the added presence of:

a catalyst comprising a compound having the formula:

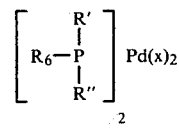

where x can be Br, I, or Cl;

and where $R_6$, $R'$ and $R''$ can be the same or different and are selected from the group consisting of phenyl, substituted phenyl and alkyl groups having from 1 to 4 carbon atoms;

and a promoter comprising cuprous iodide;

at a temperature of 20° to 200° C. and atmospheric pressure to 250 psig for one to 150 hours; to produce HBr and a bromoarylhydroxy substituted acetylene selected from the group consisting of 2-methyl-4-(3-bromophenyl)-3-butyn-2-ol and 2-methyl-4-(4-bromophenyl)-3-butyn-2-ol.

2. The process of claim 1 wherein said aryldibromide is m-dibromobenzene.

3. The process of claim 1 wherein said aryldibromide is p-dibromobenzene.

4. The process of claim 1 wherein said solvent is an amine selected from the group consisting of diethylamine and triethyamine and said catalyst is bis(triphenylphosphine) palladium dichloride.

5. The process of claim 4 wherein said amine is diethylamine.

6. The process of claim 4 wherein said amine is triethylamine.

7. The process of claim 1 wherein the molar ratio of said 2-methyl-3-butyn-2-ol to said aryldibromide is in the range of 0.95 to 1.05:1, the temperature is in the range of 50° to 125° C. and the reaction time is in the range of three to 24 hours.

* * * * *